(12) United States Patent
Wagner

(10) Patent No.: US 7,195,484 B1
(45) Date of Patent: Mar. 27, 2007

(54) ORAL PROSTHESIS FITMENT SYSTEM

(76) Inventor: Eugene C. Wagner, 1626 Chastain Pkwy. East, Pacific Palisades, CA (US) 90272

( * ) Notice: Subject to any disclaimer, the term of this patent is extended or adjusted under 35 U.S.C. 154(b) by 0 days.

(21) Appl. No.: 11/317,591

(22) Filed: Dec. 23, 2005

Related U.S. Application Data

(60) Provisional application No. 60/641,050, filed on Jan. 3, 2005.

(51) Int. Cl.
- A61C 12/02 (2006.01)
- A61C 13/225 (2006.01)
- A61K 6/00 (2006.01)

(52) U.S. Cl. .............. 433/168.1; 433/180; 523/120

(58) Field of Classification Search ........... 433/168.1, 433/180, 168, 199.1; 523/120
See application file for complete search history.

(56) References Cited

U.S. PATENT DOCUMENTS

| | | | |
|---|---|---|---|
| 4,503,116 A | 3/1985 | Lapidus | |
| 4,880,702 A * | 11/1989 | Homan et al. | 428/354 |
| 5,340,314 A * | 8/1994 | Tarvis | 433/168.1 |
| 5,880,172 A * | 3/1999 | Rajaiah et al. | 523/120 |
| 6,069,188 A | 5/2000 | Rajaiah et al. | |
| 6,276,937 B1 * | 8/2001 | Gasman | 433/168.1 |
| 6,576,712 B2 | 6/2003 | Feldstein et al. | |
| 6,638,881 B2 | 10/2003 | Lapidus | |
| 2004/0028930 A1 * | 2/2004 | Wong et al. | 428/500 |
| 2005/0228066 A1 | 10/2005 | Wong et al. | |

OTHER PUBLICATIONS

John Wiley & SOns, Inc.; 2002; Hawley's Condensed Chemical Dictionary, 14th Edition☐☐Merriam-Webster Online Dictionary.*

* cited by examiner

*Primary Examiner*—Cary E. O'Connor
(74) *Attorney, Agent, or Firm*—Seth Natter; Natter & Natter

(57) ABSTRACT

An oral prosthesis fitment system includes a wax sheet having at least one face coated with a contact or pressure sensitive adhesive. A water activated adhesive is overlaid on the contact or pressure sensitive adhesive and the sheet is contoured by modeling over and around contact surfaces of a denture plate, with the adhesive coated surface facing outward. The denture is then placed in the oral cavity and the water activated adhesive composition is either premoistened or moistened by saliva. Compressive force is then applied to assure a proper fit.

20 Claims, 1 Drawing Sheet

ORAL PROSTHESIS FITMENT SYSTEM

RELATED APPLICATIONS

This application claims the benefit of Provisional Application No. 60/641,050, filed Jan. 3, 2005.

BACKGROUND OF THE INVENTION

1. Field of the Invention

The present invention relates to systems for improving the fit, comfort and adherence of removable dental prostheses, such as dentures.

2. Antecedents of the Invention

The use of removable dental prostheses, such as dentures, generally required the application of an adhesive cream, paste or gel to assure adherence of the prosthesis in situ, irrespective of the skill of the dental practitioner and dental laboratory. Over time, even dentures which were precisely fit became lose and uncomfortable as a result of changes in gum and mucus tissue structure, often resulting in difficulty in speaking and the inability to properly masticate.

The correction of improperly fitting dentures required the patient to return to the dental practitioner for a reline, wherein material was added to the denture plate to fill the spaces between oral tissue and the previously corresponding contact surfaces of the denture plate.

Relining was an expensive and time consuming procedure, since it not only required a visit to the dental practitioner, but additionally entailed impression taking an impression and dental laboratory work. Further, the patient was denied use of the prosthesis until the reline had been completed.

Various do it yourself devices have been proposed for placement between the contact surfaces of the denture plate and the patient's corresponding oral tissue surfaces. Examples include fiber webs bonded together with a water activated adhesive sandwiched between the webs, as shown in U.S. Pat. No. 4,503,116. The disadvantages of the device disclosed in this patent included the fact that the adhesive sandwiched between the fibrous webs did not readily diffuse through the webs so as to be immediately available.

Other devices proposed for placement between the contact surfaces of a denture plate and the corresponding oral tissue surfaces of the patient included various denture adhesives, some of which were prone to oozing. The removal of residual adhesive in the oral cavity and on the denture itself were concomitant tasks. Further, several denture adhesives did not provide complete coverage, which resulted in the possible introduction of food into voids between the contact surfaces of the denture plate and the corresponding oral tissue surfaces.

SUMMARY OF THE INVENTION

An oral prosthesis fitment system comprises a stratum having a base sheet formed of wax. At least one face of the base sheet is coated with a contact or pressure sensitive adhesive and a dry water activated adhesive composition is overlaid on the contact or pressure sensitive adhesive coating on the one face.

The stratum is contoured by modeling over and around contact surfaces of a denture plate through manual manipulation, with the water activated adhesive coated surface facing outward. Self tack properties of the wax secures the stratum to the denture plate contact surfaces. Alternately a contact or pressure sensitive adhesive coating on the other face of the base sheet secures the stratum to the denture contact surfaces. Thereafter, the denture is placed in the oral cavity and the water activated adhesive composition is moistened by saliva to adhere to oral tissue and/or premoistened with water prior to placement.

Compressive force is then applied to the denture to reconfigure the thickness of the stratum to conform to the oral tissue contours, eliminating high spots and filling voids. Swelling of the water activated adhesive also serves to fill voids.

From the foregoing compendium, it will be appreciated that it is an aspect of the present invention to provide an oral prosthesis fitment system of the general character described which is not subject to the disadvantages of the antecedents of the invention aforementioned.

A feature of the present invention is to provide an oral prosthesis fitment system of the general character described which is easy to use.

A consideration of the present invention is to provide an oral prosthesis fitment system of the general character described which is hygienic and not prone to harboring bacteria.

Another aspect of the present invention is to provide an oral prosthesis fitment system of the general character described which is relatively low in cost.

A further consideration of the present invention is to provide an oral prosthesis fitment system of the general character described which assures comfort during usage of the prosthesis.

To provide an oral prosthesis fitment system of the general character described which may be installed without the assistance of dental practitioners is a still further aspect of the present invention.

Another feature of the present invention is to provide an oral prosthesis fitment system of the general character described which is well suited for mass production fabrication.

A still further consideration of the present invention is to provide an oral prosthesis fitment system of the general character described which readily adapts to the configuration of a user's oral cavity and corresponding contact surfaces of a denture plate.

Other aspects, features and considerations of the present invention in part will be obvious and in part will be pointed out hereinafter.

With these ends in view, the invention finds embodiment in the various combinations of elements, arrangements of parts and series of steps by which the said aspects, features and considerations aforementioned and certain other aspects, features and considerations are attained, all with reference to the following description and drawings and the scope of which will be more particularly pointed out and indicated in the appended claims.

BRIEF DESCRIPTION OF THE DRAWINGS

It should be noted that in the drawings, which are briefly described hereinafter, for clarity of illustration and understanding, elements of the figures have not necessarily been drawn to scale and certain elements have been omitted in some of the figures. For example, the dimensions of some of the elements may be exaggerated relative to the other elements.

In the accompanying drawings, in which are shown some of the various exemplary embodiments of the invention.

DESCRIPTION OF THE PREFERRED EMBODIMENTS

Figure 1:
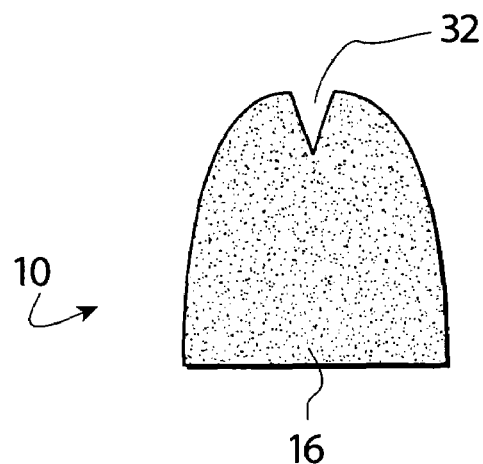
FIG. 1 is a plan view of an oral prosthesis fitment system constructed in accordance with and embodying the invention.

Referring now in detail to the drawings, the reference numeral 10 denotes generally an oral prosthesis fitment system constructed in accordance with and embodying the invention. The system 10 includes a stratum comprising a base sheet or layer 12 having an initially uniform thickness throughout. The base sheet or layer 12 is formed of a nonporous modelable material, such as a wax, for example, dental base plate wax, soft orthodontic wax or dental utility wax, which is preferably paraffin based. Among the waxes suitable for implementation as the base sheet 12 are those waxes available from Kindt-Collins Co. of Cleveland, Ohio including "sticky waxes". The base sheet 12 is preferably of a thickness in the range of 0.5 mm to 1.5 mm and has an inherently tacky surface suitable for self-adherence to contact surfaces of a denture plate as will be described hereinafter.

Figure 2:
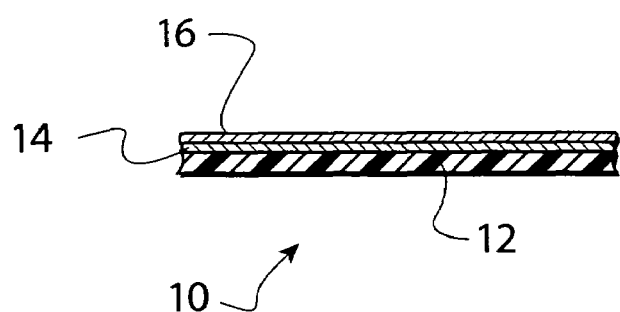
FIG. 2 is a greatly enlarged fragmentary sectional view through the oral prosthesis fitment system, the same being taken substantially along the line 2—2 of FIG. 1 and illustrating a stratum comprising a wax base sheet overlaid with a contact or pressure sensitive adhesive which is in turn, coated with a water activated adhesive.

The one surface e.g., the lower surface illustrated in FIG. 2, of the base sheet 12 remains uncoated while the opposite surface is coated with a relatively thin layer 14 of contact or pressure sensitive adhesive, such as acrylic pressure sensitive adhesives available from Rohm & Haas and employed for tapes and the like. Biomedical pressure sensitive adhesives disclosed in U.S. Pat. No. 6,576,712, incorporated herein by reference, may also be employed for the layer 14.

After the contact or pressure sensitive adhesive layer 14 has been deposited on the base sheet 12, an overlay 16 of dry water activated adhesive is applied to the surface of the contact or pressure sensitive adhesive layer 14.

The water activated adhesive overlay 16 may be comprised of polyethylene oxide, sodium alginate or mixtures thereof, or any of the adhesive formulations disclosed in U.S. Pat. No. 6,069,188, incorporated herein by reference, as well as in U.S. Pat. No. 4,503,116, also incorporated herein by reference.

The contact or pressure sensitive adhesive layer 14 serves to bond the water activated adhesive to the base sheet 12 and to bond the base sheet 12 to the contact surfaces of the oral cavity through the water activated adhesive overlay 16.

Figure 3:
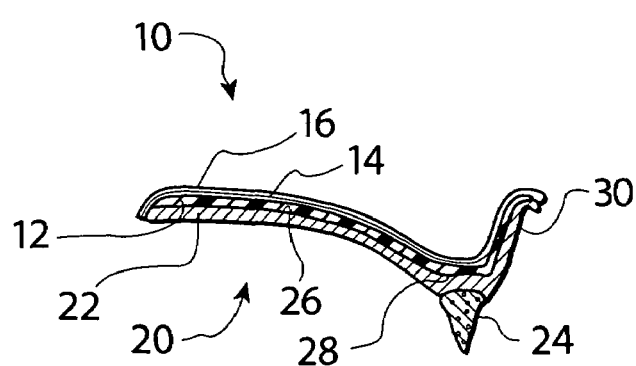
FIG. 3 is a sectional view through an upper denture illustrating the stratum modeled over contact surfaces of a denture plate and overlying the periphery, prior to trimming and insertion into the oral cavity.

With reference now to FIG. 3, wherein an upper denture 20 is illustrated as comprising a denture plate 22 and at least one prosthetic tooth 24, it will be noted that an upper surface of the denture plate 22 comprises a contact surface 26 and that the denture plate 22 is configured to conform to the wearer's palate and includes a gum line ridge 28 as well as an upwardly extending labial face 30.

In accordance with the invention, the oral prosthesis fitment system stratum is placed over the upper contact surface 26 and is modeled by digital pressure, for example, to have the unexposed lower face of the base sheet 12 placed in intimate contact with the upper contact surface 26. It should be noted, from an examination of FIG. 1, that the fitment system stratum can be configured in the shape of a dental arch, having a "V" notch 32 at its apex, such that when modeled over the contact surface 26, the base sheet 12 will not fold over itself, i.e. will not overlap.

Excess material which extends over the periphery of the denture plate 22, for example, the material overlapping the upper edge of the labial face 30 illustrated in FIG. 3, may be trimmed with a knife or scissors.

Thereafter, the denture 20 is placed in the oral cavity and against the wearer's palate. It should be noted that the surface of the exposed water activated adhesive overlay 16 may be premoistened under tap water. The tap water and/or saliva within the palate serves to activate the water-activated adhesive in the overlay 16 and assures adhesion of the denture to the palate.

Additionally, the denture may be forced upwardly into the palate by manual pressure or biting, for example, to redistribute the thickness of the stratum to thereby remove any high spots of uneven contact and redistribute the material to fill any voids.

It should also be noted that the laminate may be formed or cut into strips for use, in securing a lower or partial dental prosthesis or optionally applied in strips to the contact surface 26 of an upper denture plate 22.

Figure 4:
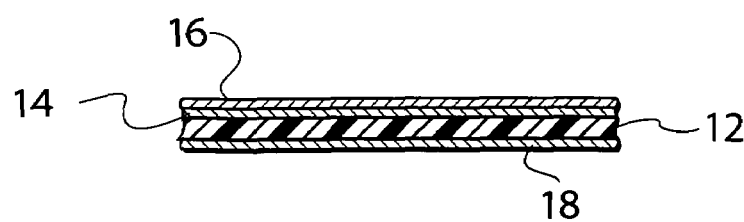
FIG. 4 is a greatly enlarged fragmentary sectional view through an alternate embodiment of the fitment system, similar to FIG. 2 wherein both faces of a base sheet are overlaid with contact or pressure sensitive adhesive.

In the alternate embodiment illustrated in FIG. 4, the stratum is formed with an upper face of the wax base sheet 12 covered with an upper face of the wax base sheet 12 covered with a layer 14 of contact or pressure sensitive adhesive which in turn receives an overlay 16 of water activated adhesive. Additionally, a lower face of the base sheet 12 is coated with a contact or pressure sensitive adhesive layer 18 for adhesion of the base sheet 12 to the contact surfaces 26.

It should also be appreciated that the oral prosthesis fitment system of the present invention may be employed without the requirement for the overlay 16 of dry water activated adhesive in instances wherein the selected contact or pressure sensitive adhesive is capable of adhering to the moist oral tissue of the wearer's palate and/or mandibular oral tissue contact surfaces.

Because the wax base sheet 12 is nonporous, it can easily be sanitized or sterilized prior to use and is not prone to harboring bacteria during usage, thus promoting oral hygiene and reducing an oral malodor contributory factor.

Thus it will be seen that there is provided an oral applicator which achieves the various aspects, features and considerations of the present invention and which is well adapted to meet the conditions of practical usage.

Since various possible embodiments might be made of the present invention and since various changes might be made in the exemplary embodiments set forth herein without departing from the spirit of the invention, is to be understood that all matter herein described or shown in the accompanying drawings is to be interpreted as illustrative and not in a limiting sense.

Having thus described the invention, there is claimed as new and desired to be secured by Letters Patent:

1. A fitment system for a removable oral prosthesis, the fitment system comprising a stratum having a base layer configured for effective application between contact surfaces of an oral prosthesis and corresponding oral tissue surfaces of a wearer, the base layer comprising a nonporous sheet consisting of wax, the base layer having opposed faces, at least one face of the base layer including a layer of contact or pressure sensitive adhesive.

2. A fitment system for a removable oral prosthesis as constructed in accordance with claim 1 wherein the layer of contact or pressure sensitive adhesive is overlaid with a water activated adhesive.

3. A method of fitting a removable oral prosthesis with a fitment system as constructed in accordance with claim 2, the method comprising the steps of:
   a) registering the other face of the base layer with contact surfaces of the oral prosthesis,
   b) modeling the base layer against the contact surfaces by manual manipulation, and
   c) inserting the oral prosthesis in the oral cavity.

4. A method of fitting a removable oral prosthesis as in accordance with claim 3 further including the step of:
   d) moistening the water activated adhesive.

5. A method of fitting a removable oral prosthesis in accordance with claim 4 further including the step of:
   e) moistening the water activated adhesive prior to performing step c).

6. A fitment system for a removable oral prosthesis as constructed in accordance with claim 1 wherein the base layer is in the order of 0.5 mm and 1.5 mm in thickness.

7. A fitment system for a removable oral prosthesis as constructed in accordance with claim 1 wherein the thickness of the stratum is substantially uniform.

8. A fitment system for a removable oral prosthesis as constructed in accordance with claim 1 wherein both faces of the base layer have a layer of contact or pressure sensitive adhesive.

9. A fitment system for a removable oral prosthesis as constructed in accordance with claim 1 wherein the base layer is modelable.

10. A fitment system for a removable oral prosthesis as constructed in accordance with claim 1 wherein the thickness of the base layer is reconfigurable as a result of the application of compressive force.

11. A fitment system for a removable oral prosthesis as constructed in accordance with claim 9 further including an oral prosthesis, the oral prosthesis having a contact surface, the base layer being modeled over the contact surface.

12. A fitment system for a removable oral prosthesis as constructed in accordance with claim 11 wherein the other face of the base layer is in abutting contact with the oral prosthesis contact surface.

13. A method of fitting a removable oral prosthesis with a fitment system as constructed in accordance with claim 1, the method comprising the steps of:
   a) registering the other face of the base layer with contact surfaces of the oral prosthesis,
   b) modeling the base layer against the contact surfaces by manual manipulation, and
   c) inserting the oral prosthesis in the oral cavity.

14. A removable oral prosthesis, the prosthesis comprising a plate, at least one prosthetic tooth secured to the plate, the plate having a contact surface, a nonporous sheet consisting of wax configured to overlie the contact surface, the wax sheet being modeled to the contour of the contact surface and abutting the contact surface, the wax sheet having an exposed adhesive coating for adherence to contact surfaces of the wearer's oral cavity.

15. A removable oral prosthesis as constructed in accordance with claim 14 further including a contact or pressure sensitive adhesive coating positioned between the wax sheet and the exposed adhesive coating.

16. A removable oral prosthesis as constructed in accordance with claim 14 further including an adhesive coating positioned between the wax sheet and the contact surface of the plate.

17. A removable oral prosthesis as constructed in accordance with claim 14 wherein the exposed adhesive coating comprises a water activated adhesive.

18. A method of securing a removable oral prosthesis comprising a plate having a contact surface and at least one prosthetic tooth, the method comprising the steps of:
   a) providing a nonporous sheet consisting of wax and having an adhesive coating on at least one face, the nonporous sheet being configured to overlie the contact surface of the plate,
   b) modeling the other face of the nonporous sheet against the contour of the contact surface of the plate,
   c) inserting the oral prosthesis in the oral cavity, and
   d) applying a compressive force against the oral prosthesis.

19. A method of securing a removable oral prosthesis in accordance with claim 18 wherein the adhesive coating comprises a contact or pressure sensitive adhesive, the method including the further step of applying a water activated adhesive over the pressure sensitive adhesive coating before practicing step b).

20. A method of securing a removable oral prosthesis in accordance with claim 18 wherein the other face of the nonporous sheet is provided with an adhesive coating and step b) includes the step of adhering the other face against the contour of the contact surface with the adhesive coating.

* * * * *